(12) United States Patent  
Christensen et al.

(10) Patent No.: US 10,426,685 B2  
(45) Date of Patent: Oct. 1, 2019

(54) MOBILE PATIENT BED

(71) Applicant: OPTIMEDICA CORPORATION, Santa Ana, CA (US)

(72) Inventors: Steven S. Christensen, Fremont, CA (US); Antonio D. Lucero, Fresno, CA (US); Brian Riley, San Francisco, CA (US); Eric B. Lafay, Sunnyvale, CA (US); David D. Scott, Oakland, CA (US)

(73) Assignee: OPTIMEDICA CORPORATION, Santa Ana, CA (US)

( * ) Notice: Subject to any disclaimer, the term of this patent is extended or adjusted under 35 U.S.C. 154(b) by 0 days.

(21) Appl. No.: 15/904,151

(22) Filed: Feb. 23, 2018

(65) Prior Publication Data

US 2018/0177659 A1    Jun. 28, 2018

Related U.S. Application Data

(63) Continuation of application No. 14/930,542, filed on Nov. 2, 2015, now Pat. No. 9,901,503.

(51) Int. Cl.
*A61G 13/10* (2006.01)
*A61G 13/08* (2006.01)
(Continued)

(52) U.S. Cl.
CPC ........... *A61G 13/105* (2013.01); *A61G 1/017* (2013.01); *A61G 1/0243* (2013.01); *A61G 13/08* (2013.01);
(Continued)

(58) Field of Classification Search
CPC ..................................................... G05B 15/02
(Continued)

(56) References Cited

U.S. PATENT DOCUMENTS

| 5,444,882 A | 8/1995 | Andrews et al. |
|---|---|---|
| 5,455,975 A | 10/1995 | Foster |

(Continued)

FOREIGN PATENT DOCUMENTS

| CN | 201005929 Y | 1/2008 |
|---|---|---|
| CN | 201049058 Y | 4/2008 |

(Continued)

OTHER PUBLICATIONS

International Search Report and Written Opinion for Application No. PCT/US2015/058662, dated Aug. 12, 2016, 10 pages.

*Primary Examiner* — David Luo
(74) *Attorney, Agent, or Firm* — Johnson & Johnson Surgical Vision, Inc.

(57) ABSTRACT

A mobile patient bed may be used for moving a patient between at least two locations during a medical procedure. The mobile patient bed may comprise an interface configured to selectively couple the mobile patient bed to at least one medical system and at least one processor configured to receive a medical system command via the interface and process the medical system command when the mobile patient bed is coupled to the at least one medical system, receive and process a user command when the mobile patient bed is not coupled to the at least one medical system, and refrain from processing the user command when the mobile patient bed is coupled to the at least one medical system. The mobile patient bed may also comprise a seat and a plurality of motors configured to independently position the seat along a plurality of axes.

19 Claims, 11 Drawing Sheets

(51) Int. Cl.
*G05B 15/02* (2006.01)
*G16H 40/63* (2018.01)
*A61G 1/017* (2006.01)
*A61G 1/02* (2006.01)
*A61G 13/12* (2006.01)

(52) U.S. Cl.
CPC ............ *A61G 13/121* (2013.01); *G05B 15/02* (2013.01); *G16H 40/63* (2018.01); *A61G 2203/10* (2013.01); *A61G 2203/14* (2013.01); *A61G 2210/00* (2013.01)

(58) Field of Classification Search
USPC ....................................................... 318/3, 34
See application file for complete search history.

(56) References Cited

U.S. PATENT DOCUMENTS

| | | |
|---|---|---|
| 5,475,884 A | 12/1995 | Kirmse et al. |
| 5,615,430 A | 4/1997 | Nambu et al. |
| 5,720,894 A | 2/1998 | Neev et al. |
| 5,781,949 A | 7/1998 | Weismiller et al. |
| 5,957,915 A | 9/1999 | Trost |
| 5,971,432 A * | 10/1999 | Gagnon ................ B60N 2/002 180/268 |
| 5,984,916 A | 11/1999 | Lai |
| 5,996,149 A | 12/1999 | Heimbrock et al. |
| 6,019,472 A | 2/2000 | Koester et al. |
| 6,071,228 A | 6/2000 | Speraw et al. |
| 6,108,838 A | 8/2000 | Connolly et al. |
| 6,226,816 B1 | 5/2001 | Webster et al. |
| 6,237,172 B1 | 5/2001 | Morgan, Sr. |
| 6,260,220 B1 | 7/2001 | Lamb et al. |
| 6,266,831 B1 | 7/2001 | Heimbrock |
| 6,398,409 B1 | 6/2002 | Brooks |
| 6,454,761 B1 | 9/2002 | Freedman |
| 6,459,923 B1 | 10/2002 | Plewes et al. |
| 6,493,568 B1 | 12/2002 | Bell et al. |
| 6,526,609 B2 | 3/2003 | Wong |
| 6,564,406 B2 | 5/2003 | Vansteenburg et al. |
| 6,585,206 B2 | 7/2003 | Metz et al. |
| 6,622,324 B2 | 9/2003 | Vansteenburg et al. |
| 6,640,364 B1 | 11/2003 | Josephson et al. |
| 6,725,483 B2 | 4/2004 | Gallant et al. |
| 6,776,527 B1 | 8/2004 | Tybinkowski et al. |
| 6,782,571 B1 | 8/2004 | Josephson et al. |
| 6,822,571 B2 | 11/2004 | Conway |
| 6,862,762 B1 | 3/2005 | Johnson et al. |
| 6,874,181 B1 | 4/2005 | Connolly et al. |
| 7,018,157 B2 | 3/2006 | Gallant et al. |
| 7,020,917 B1 | 4/2006 | Kolody et al. |
| 7,024,711 B1 | 4/2006 | Stasney et al. |
| 7,055,195 B2 | 6/2006 | Roussy |
| 7,073,219 B2 | 7/2006 | Poulin et al. |
| 7,219,379 B2 | 5/2007 | Krywiczanin et al. |
| 7,243,386 B2 | 7/2007 | Gallant et al. |
| 7,322,059 B2 | 1/2008 | Hornbach |
| 7,398,571 B2 | 7/2008 | Souke et al. |
| 7,426,760 B2 | 9/2008 | Vrzalik |
| 7,523,514 B2 | 4/2009 | Salt et al. |
| 7,568,247 B2 | 8/2009 | Strobel et al. |
| 7,641,623 B2 | 1/2010 | Biondo et al. |
| 7,644,457 B2 | 1/2010 | Hensley et al. |
| 7,655,002 B2 | 2/2010 | Myers et al. |
| 7,702,481 B2 * | 4/2010 | Dionne .................. A61G 7/015 702/150 |
| 7,717,907 B2 | 5/2010 | Ruiz et al. |
| 7,737,827 B2 | 6/2010 | Perkins et al. |
| 7,751,375 B2 | 7/2010 | Perkins et al. |
| 7,768,949 B2 | 8/2010 | Perkins et al. |
| 7,882,582 B2 * | 2/2011 | Kappeler ................ A61G 7/018 5/600 |
| 7,908,690 B2 | 3/2011 | Luginbuhl et al. |
| 7,913,337 B1 | 3/2011 | Masson |
| 7,971,289 B2 | 7/2011 | Payne et al. |
| 8,005,686 B2 | 8/2011 | Smith |
| 8,117,695 B2 | 2/2012 | Paz et al. |
| 8,258,973 B2 | 9/2012 | Newkirk |
| 8,262,646 B2 | 9/2012 | Frey et al. |
| 8,264,342 B2 | 9/2012 | Blair et al. |
| 8,266,741 B2 | 9/2012 | Penninger et al. |
| 8,272,892 B2 | 9/2012 | McNeely et al. |
| 8,286,282 B2 | 10/2012 | Kummer et al. |
| 8,336,134 B2 | 12/2012 | Jelinek |
| 8,341,777 B2 | 1/2013 | Hensley et al. |
| 8,341,779 B2 | 1/2013 | Hornbach et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 8,421,606 B2 | 4/2013 | Collins, Jr. et al. |
| 8,474,072 B2 * | 7/2013 | O'Keefe ................ A61G 7/018 340/286.07 |
| 8,615,827 B2 | 12/2013 | Newkirk et al. |
| 8,621,688 B2 | 1/2014 | Andrienko |
| 8,689,376 B2 | 4/2014 | Becker et al. |
| 8,707,483 B2 | 4/2014 | Richards et al. |
| RE44,884 E | 5/2014 | Lambarth |
| 8,713,727 B2 | 5/2014 | Heimbrock et al. |
| 8,745,786 B2 | 6/2014 | Andrienko et al. |
| 8,752,220 B2 | 6/2014 | Soderberg et al. |
| 8,864,205 B2 | 10/2014 | Lemire et al. |
| 8,898,830 B2 | 12/2014 | Hushek |
| 8,973,186 B2 | 3/2015 | Bhai |
| 8,984,685 B2 | 3/2015 | Robertson et al. |
| 9,072,643 B2 | 7/2015 | Hines |
| 9,265,680 B2 | 2/2016 | Sharps et al. |
| 9,358,169 B2 | 6/2016 | Ottenweller et al. |
| 2005/0125899 A1 | 6/2005 | Hanson et al. |
| 2006/0026761 A1 | 2/2006 | Falbo |
| 2007/0039101 A1 | 2/2007 | Luginbuhl et al. |
| 2007/0066866 A1 | 3/2007 | Noguchi et al. |
| 2007/0238949 A1 | 10/2007 | Wang et al. |
| 2008/0147442 A1 | 6/2008 | Warner et al. |
| 2009/0089930 A1 | 4/2009 | Benzo et al. |
| 2009/0094745 A1 | 4/2009 | Benzo et al. |
| 2010/0031443 A1 | 2/2010 | Georgiev et al. |
| 2010/0172468 A1 | 7/2010 | Gregerson |
| 2011/0140869 A1 | 6/2011 | Liu et al. |
| 2011/0154569 A1 | 6/2011 | Wiggers et al. |
| 2011/0181394 A1 | 7/2011 | Blair |
| 2011/0319873 A1 | 12/2011 | Raksi et al. |
| 2011/0319875 A1 | 12/2011 | Loesel et al. |
| 2012/0089419 A1 | 4/2012 | Huster et al. |
| 2012/0124744 A1 | 5/2012 | Hornbach et al. |
| 2012/0259248 A1 | 10/2012 | Receveur |
| 2013/0091631 A1 | 4/2013 | Hayes et al. |
| 2013/0110094 A1 | 5/2013 | Wellhoefer et al. |
| 2013/0152307 A1 | 6/2013 | Bennett-Guerrero |
| 2014/0020179 A1 | 1/2014 | Brougham et al. |
| 2014/0059770 A1 | 3/2014 | Williamson et al. |
| 2014/0076644 A1 | 3/2014 | Derenne et al. |
| 2014/0080413 A1 | 3/2014 | Hayes et al. |
| 2014/0232551 A1 | 8/2014 | Huster |
| 2014/0255890 A1 | 9/2014 | Kovach et al. |
| 2014/0259411 A1 | 9/2014 | Sunazuka et al. |
| 2014/0259414 A1 | 9/2014 | Hayes et al. |
| 2014/0266643 A1 | 9/2014 | Receveur et al. |
| 2015/0157520 A1 | 6/2015 | Shiery et al. |
| 2015/0186611 A1 | 7/2015 | George et al. |
| 2015/0216746 A1 | 8/2015 | Dirauf et al. |
| 2015/0297432 A1 | 10/2015 | Poulos et al. |
| 2016/0045383 A1 | 2/2016 | Soo |
| 2016/0136022 A1 | 5/2016 | Johnson et al. |

FOREIGN PATENT DOCUMENTS

| | | |
|---|---|---|
| CN | 201537134 U | 8/2010 |
| CN | 201542836 U | 8/2010 |
| CN | 201624907 U | 11/2010 |
| CN | 101785735 B | 7/2011 |
| CN | 201978101 U | 9/2011 |
| CN | 202128643 U | 2/2012 |
| CN | 202207160 U | 5/2012 |

(56) References Cited

FOREIGN PATENT DOCUMENTS

| | | |
|---|---|---|
| CN | 202223448 U | 5/2012 |
| CN | 202283277 U | 6/2012 |
| CN | 103431959 A | 12/2013 |
| CN | 203341745 U | 12/2013 |
| CN | 203524897 U | 4/2014 |
| CN | 203724393 U | 7/2014 |
| CN | 103961233 A | 8/2014 |
| CN | 103976830 A | 8/2014 |
| CN | 203790156 U | 8/2014 |
| CN | 203790237 U | 8/2014 |
| CN | 203815733 U | 9/2014 |
| CN | 104287909 A | 1/2015 |
| CN | 204192957 U | 3/2015 |
| CN | 204307003 U | 5/2015 |
| CN | 204446329 U | 7/2015 |
| CN | 104856808 A | 8/2015 |
| CN | 104921877 A | 9/2015 |
| CN | 105193569 A | 12/2015 |
| CN | 204951417 U | 1/2016 |
| CN | 204971920 U | 1/2016 |
| CN | 205054620 U | 3/2016 |
| EP | 0841886 B1 | 6/2005 |
| EP | 1370178 B1 | 8/2005 |
| EP | 1635755 B1 | 11/2007 |
| EP | 2484325 A2 | 8/2012 |
| EP | 2591759 A1 | 5/2013 |
| EP | 2705822 A1 | 3/2014 |
| EP | 2227210 B1 | 8/2014 |
| EP | 2784709 A2 | 10/2014 |
| GB | 2527454 A | 12/2015 |
| JP | H08112244 A | 5/1996 |
| JP | 2000296157 A | 10/2000 |
| JP | 2004329525 A | 11/2004 |
| JP | 2013106676 A | 6/2013 |
| JP | 5707479 B2 | 4/2015 |
| JP | 5789051 B2 | 10/2015 |
| KR | 101448201 B1 | 10/2014 |
| WO | 9427544 A2 | 12/1994 |
| WO | 9913766 A1 | 3/1999 |
| WO | 0170167 A2 | 9/2001 |
| WO | 2008103177 A1 | 8/2008 |
| WO | 2014090253 A1 | 6/2014 |
| WO | 2014148755 A1 | 9/2014 |
| WO | 2014164248 A1 | 10/2014 |
| WO | 2014172621 A2 | 10/2014 |
| WO | 2015032003 A1 | 3/2015 |
| WO | 2015073792 A2 | 5/2015 |
| WO | 2016020883 A1 | 2/2016 |
| WO | 2016039417 A1 | 3/2016 |

\* cited by examiner

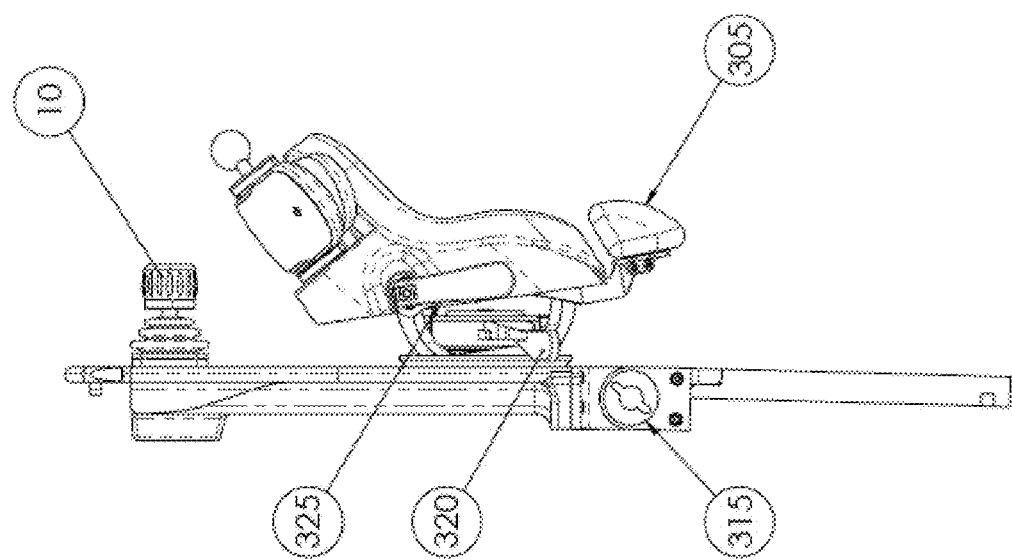

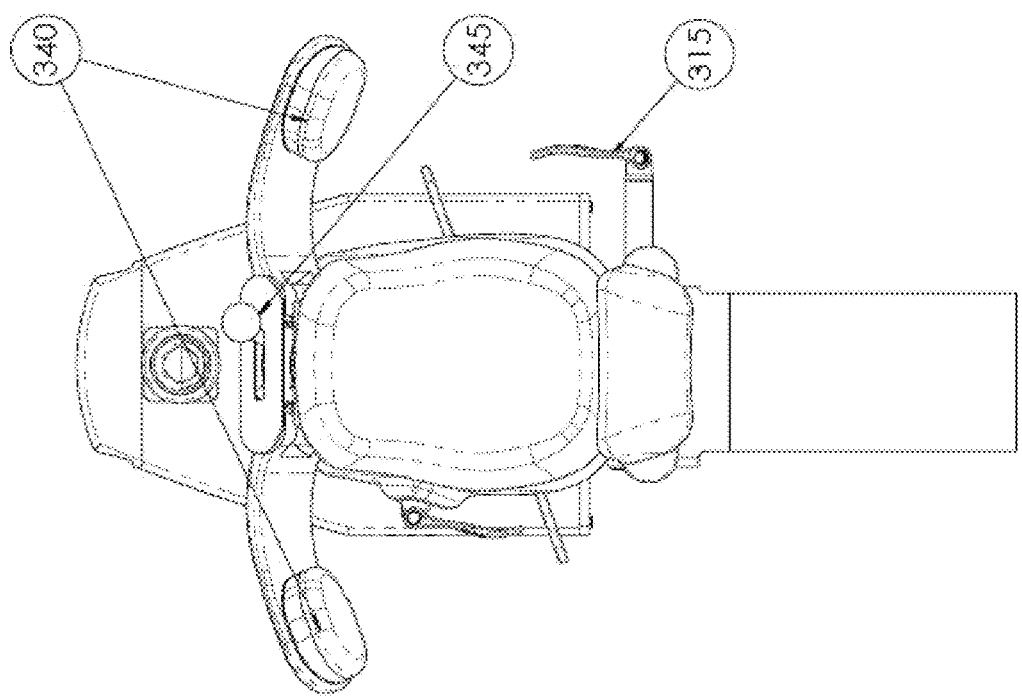

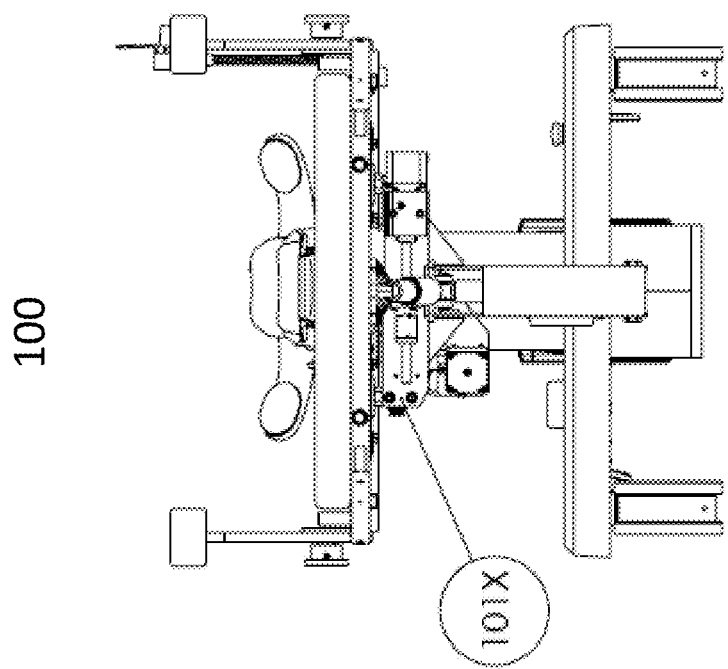

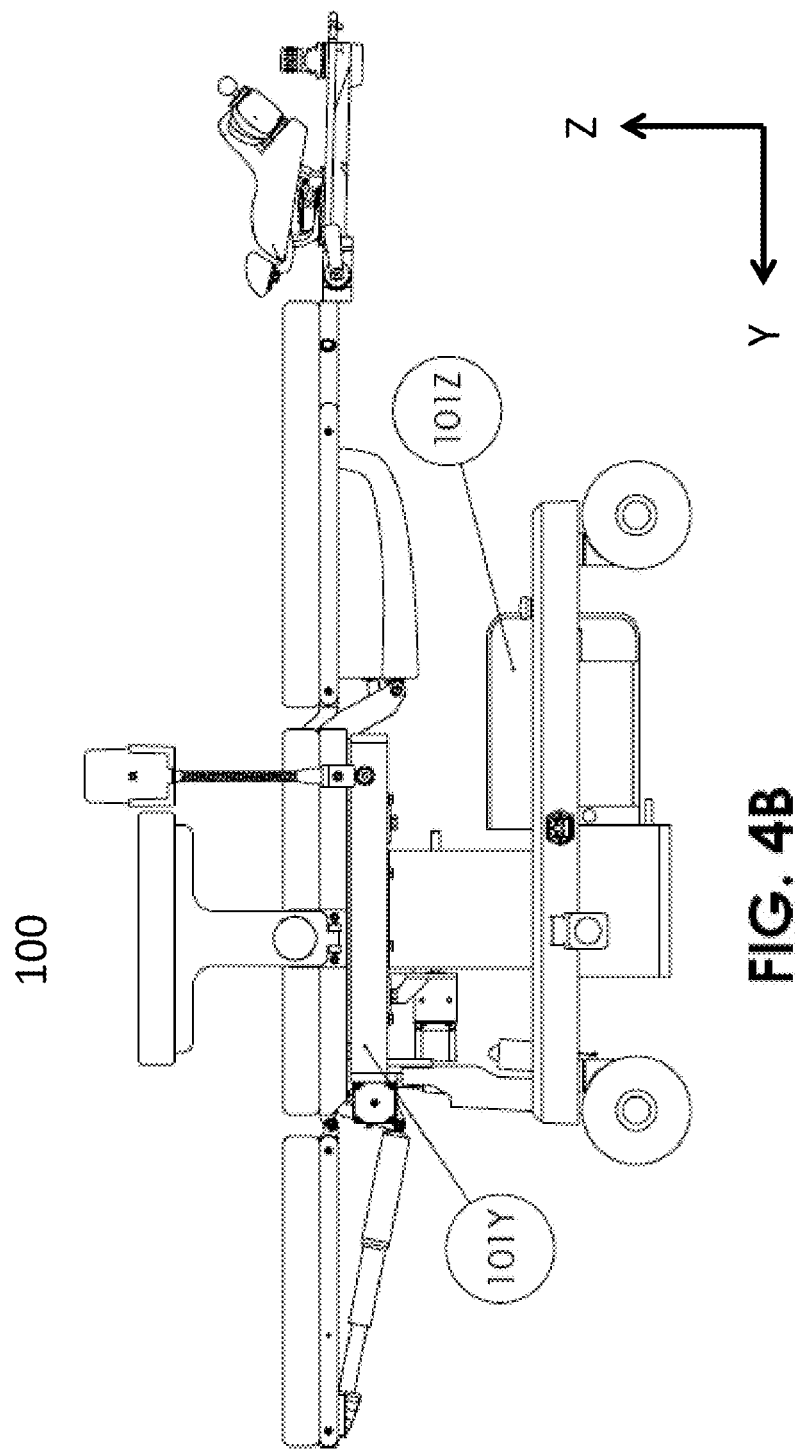

MOBILE PATIENT BED

The present application is a continuation of and claims priority under 35 U.S.C. § 120 to U.S. patent application Ser. No. 14/930,542, filed Nov. 2, 2015, the entire content of which is incorporated by reference herein as if fully set forth.

CROSS-REFERENCE TO RELATED APPLICATIONS

The subject matter of the present disclosure is related to the following patent applications: U.S. patent application Ser. No. 14/256,307, filed on Apr. 18, 2014, entitled "CORNEAL TOPOGRAPHY MEASUREMENT AND ALIGNMENT OF CORNEAL SURGICAL PROCEDURES," U.S. application Ser. No. 12/048,182, filed 3 Mar. 2008, entitled "METHOD AND APPARATUS FOR CREATING INCISIONS TO IMPROVE INTRAOCULAR LENS PLACEMENT"; U.S. application Ser. No. 12/048,186, filed 13 Mar. 2008, entitled "METHOD AND APPARATUS FOR CREATING OCULAR SURGICAL AND RELAXING INCISIONS"; U.S. Application Ser. No. 61/722,064, filed 02 Nov. 2012, entitled "LASER EYE SURGERY SYSTEM CALIBRATION"; U.S. patent application Ser. No. 14/199,087, U.S. patent application Ser. No. 14/199,087 filed Mar. 15, 2014, entitled "MICROFEMTOTOMY METHODS AND SYSTEMS"; U.S. Ser. No. 61/813,172, filed Apr. 17, 2013, entitled "LASER FIDUCIALS FOR ALIGNMENT IN CATARACT SURGERY. The entire disclosures of the above-referenced patent applications are incorporated herein by reference, and are suitable for combination according to embodiments disclosed herein.

FIELD OF INVENTION

Embodiments of this invention relate generally to patient beds for medical procedures, and more particularly, to systems and methods providing mobile patient beds for medical and/or surgical procedures.

BACKGROUND

Many medical procedures require a patient to lie or sit on a bed. Some medical procedures, such as ophthalmic laser surgery, require a patient to either lie down, and/or sit on a bed during one or more stages of the procedure. For example, prior to ophthalmic surgery, a patient may be prepped for surgery and have his or her eye(s) measured and either while sitting or lying down on a bed. Later, the patient may lie down while undergoing laser treatment for various procedures, such as corneal flap creation, laser-assisted in situ keratomileusis (LASIK), or capsulotomy and lens fragmentation for treatment of cataract. The patient may also need to lie down during operation procedures such as phacoemulsification, cataract removal, and intraocular lens (IOL) implantation. Following surgery, the patient may lie on the bed to recuperate.

Most beds that are used with surgical laser systems tend to be large and heavy, and fixed onto the system. Hence, they can be cumbersome, and require significant space for storage. Beds that are fixed to the system also add time to the work flow of the procedures, as while one patient is undergoing laser treatment, another cannot get prepped, and/or recuperate using the same bed or system. On the other hand, moving a patient from different beds while undergoing surgery and/or other medical procedure to accommodate the work flow can also add more time to the procedure. Therefore, there is a need for improved systems and methods for patient beds for medical procedures.

SUMMARY OF THE DESCRIPTION

Hence, to obviate one or more problems due to limitations and disadvantages of the related art, this disclosure provides embodiments of systems and methods for a mobile patient bed for moving a patient between at least two locations during a medical procedure. The mobile patient bed may comprise a communication device (e.g., a Bluetooth transceiver or other wireless transceiver) configured to selectively couple the mobile patient bed to at least one medical system (e.g., a laser eye surgery system). The mobile patient bed may comprise at least one processor configured to receive a medical system command via the communication device and process the medical system command when the mobile patient bed is coupled to the at least one medical system, receive and process a user command (e.g., via at least one user control) when the mobile patient bed is not coupled to the at least one medical system, and refrain from processing the user command when the mobile patient bed is coupled to the at least one medical system. The mobile patient bed may be coupled to the medical system in at least one of the locations and not coupled to the medical system in at least another one of the locations.

The mobile patient bed may comprise a seat and a plurality of motors. The plurality of motors may be configured to position the seat along a first axis that is longitudinal with respect to the bed, a second axis substantially perpendicular to the first axis, and a third axis substantially perpendicular to the first and second axes, wherein the positioning of the seat along each axis is independent of the positioning of each other axis, respectively, and wherein the positioning of the seat is performed in response to the processed medical system command or the processed user command. For example, the plurality of motors may be configured to position the seat in a Trendelenburg position.

The mobile patient bed may comprise a plurality of actuators configured to position the bed and/or portions thereof. For example, the mobile patient bed may include a first axis actuator, a second axis actuator, a third axis actuator, a foot rest actuator, a Trendelenburg actuator, and/or a back rest actuator. In some embodiments, the first axis, second axis, and third axis actuators may move the seat along an x axis, a y axis, and a z axis.

The mobile patient bed may further comprise a headrest configured to pivot about a fourth axis substantially parallel to the first axis and to move along the fourth axis, a fifth axis substantially perpendicular to the fourth axis, and a sixth axis substantially perpendicular to the fourth and fifth axes, wherein the positioning of the headrest along each axis is independent of the positioning of each other axis, respectively.

The mobile patient bed may further comprise a plurality of casters. At least one of the casters may be lockable with respect to transverse motion along the ground to allow the mobile patient bed to pivot about a pivoting axis perpendicular to the ground. A brake configured to lock at least one of the casters from rotation may be included.

The medical system may be configured to determine a relative location of the at least one mobile patient bed via a signal received from the communication device of the at least one mobile patient bed. For example, the medical system may determine the position of the at least one mobile patient bed based on radio communications with the at least one mobile patient bed. In some embodiments, the medical system may use a plurality of receivers to receive a communication from the at least one mobile patient bed, and triangulate the position of the bed based on differences in times at which the communication is received by each receiver. The medical system may also be configured to assign a separate identity to each at least one mobile patient bed, for example during initial setup of the mobile patient bed with a laser system.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIGS. 3A-3C show a mobile patient bed headrest, in accordance with many embodiments.

FIGS. 4A-4B show mobile patient bed motors, in accordance with many embodiments.

DETAILED DESCRIPTION OF SEVERAL EMBODIMENTS

Mobile patient beds such as the embodiments described herein may be used to support a patient during various stages of one or more medical procedures and move the patient between the stages. For example, in ophthalmic laser surgery, the bed may be taken from a surgery prep area to a laser surgery suite, from the laser surgery suite to a surgery suite or operating room, and from the surgery suite or operating room to a recovery area. In each area, the bed may be used to provide and/or support various surgical functions. Specific bed use examples may include cataract surgery for removal of the crystalline lens (e.g., anterior capsulotomy, phaco-fragmentation, and/or creation of single plane and multi-plane arcuate cuts/incisions in the cornea, each of which may be performed either individually or consecutively during the same cataract surgery procedure), and/or to transport and to position the patient for surgical removal of the crystalline lens and implantation of an IOL. Ophthalmic laser surgery is presented as an exemplary medical procedure for use with the bed herein, but mobile patient bed embodiments may be used for other procedures with similar and/or different stages as well (e.g., dental procedures, other surgical or medical procedures, etc.).

For example, the mobile patient bed may be used as a patient support system with a precision laser system for cataract surgery. The mobile patient bed may be located next to and wirelessly connected to the laser system to position a patient for laser cataract surgery. Once the laser procedure is completed, the mobile patient bed may be either rotated out from under the laser system to perform surgical removal of the crystalline lens and to implant an IOL or disconnected from the laser system to transport the patient to a surgery suite. The mobile patient bed may be fully functional when not attached to the laser system to transport and position a patient for surgical removal of the crystalline lens and implantation of an IOL. When positioned under the laser system, the mobile patient bed may be a fully integrated sub-system of the laser system.

In addition to being movable from place to place, the mobile patient bed may be free to rotate about one or more casters (e.g., the front right caster located near the patient's right foot in some embodiments) about a vertical axis while the one or more caster wheels are locked from rotating/rolling.

Mobile Patient Bed

Figure 1:
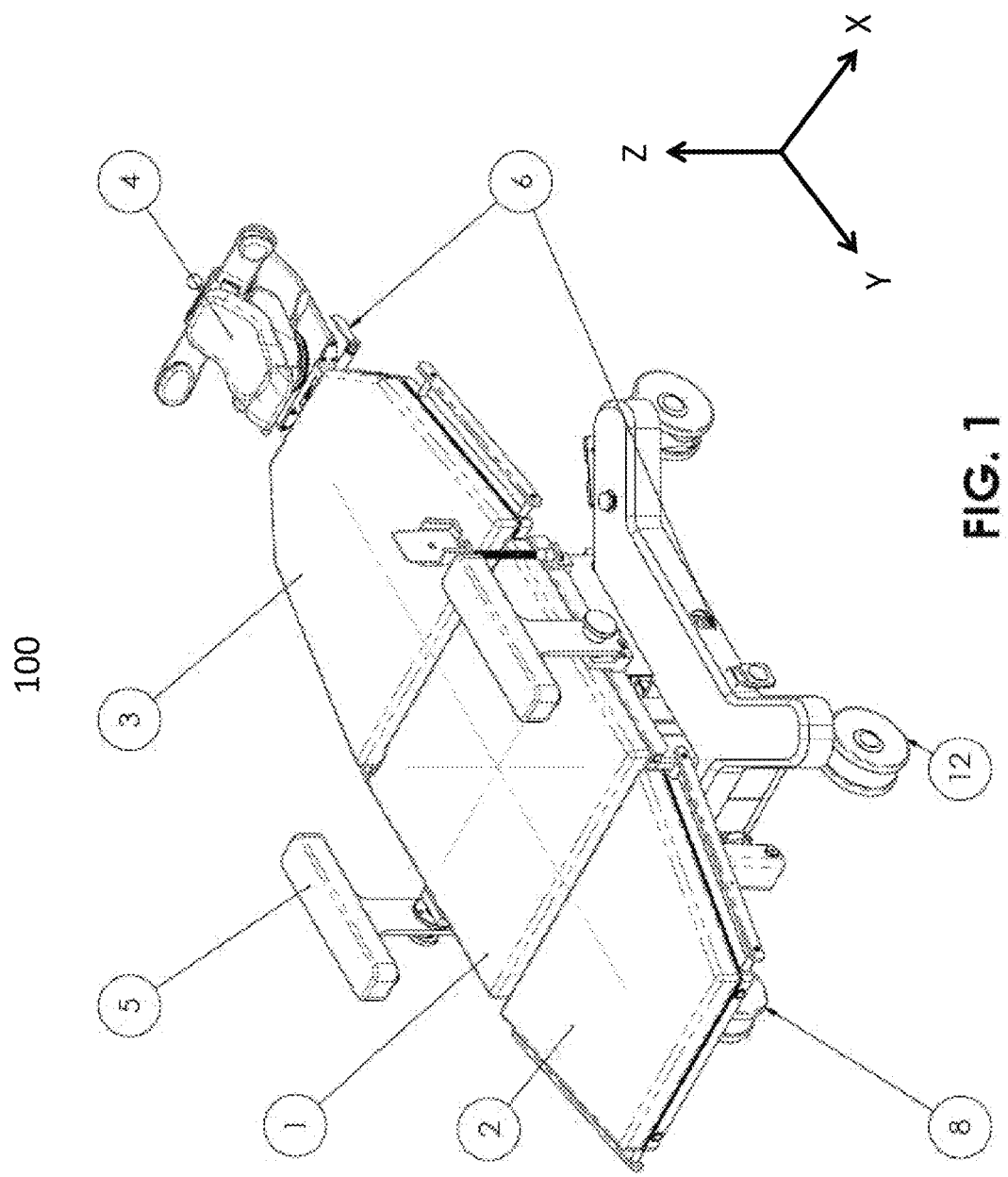
FIG. 1 is a perspective view of a mobile patient bed, in accordance with many embodiments.

FIG. 1 is a mobile patient bed 100 according to an embodiment of the invention. The mobile patient bed 100 may include a patient seat 1, a patient footrest 2, a patient backrest 3, a patient headrest 4, and/or patient armrests 5. The mobile patient bed 100 may include casters with brakes 8, one or more of which may be locking casters 12, and emergency stop controls (e.g., an emergency stop switch, not shown). The mobile patient bed 100 may include operator handles and controls 6 (e.g., which may include foot pedals and/or a control pendant), and/or a control joystick 10 which may allow the operator to interact with control electronics and electrical components (not shown) which may be housed inside the mobile patient bed 100. For example, the mobile patient bed 100 control electronics and electrical components may be located in a metal enclosure under the patient seat 1 and in the mobile patient bed 100 base. The internal components may include communication link components (e.g., wired and/or wireless networking transceivers, hardware, and software) to allow the mobile patient bed 100 to be controlled by remote laser and/or surgical systems.

The mobile patient bed 100 may be controlled via the user inputs (e.g., controls 6, joystick 10, and/or pendant) and/or via the communication link to perform a variety of actions. For example a user and/or laser system may command the mobile patient bed 100 to adjust X, Y, and/or Z-position of the mobile patient bed 100, articulation of the seat 1, footrest 2, backrest 3, and/or headrest 4. In some embodiments, some of these articulations may be manual (e.g., headrest 4) and/or may be independently controlled at the mobile patient bed 100 only, rather than controllable by the laser system (e.g., footrest 2, backrest 3, and/or headrest 4). The mobile patient bed 100 pivot wheel lock, total caster locks, and/or X-Y-Z position may also be controlled via pre-programmed buttons located on the pendant. Controls 6 and/or other components of the mobile patient bed 100 capable of displaying information to a user may provide an indication of mobile patient bed 100 battery status.

The joystick 10 may be, for example, a hard wired 3-axis joystick control. The joystick may provide user inputs to the laser system to control the mobile patient bed 100 motion in the X, Y, and Z axes. The control joystick 10 may be active and functional only when the mobile patient bed 100 is connected to the laser system through the wireless connection. While the mobile patient bed 100 is being utilized as a standalone device, the joystick 10 may be deactivated. Likewise, while the mobile patient bed 100 is connected to the laser system, other controls 6 may be deactivated.

The mobile patient bed 100 may be equipped with a latching emergency stop switch. Pushing the emergency stop switch may disable electrical power to the mobile patient bed 100. A twist of the emergency stop switch may release the emergency stop switch. The emergency stop switch may be located on the top surface of the mobile patient bed 100 base enclosure. Other configurations for an emergency stop switch aside from the one described may also be possible. For example, some embodiments may allow an emergency stop command to be issued via wireless communication to the mobile patient bed 100 (e.g., from the laser system).

The mobile patient bed 100 may sit on a plurality of casters (e.g., four) 8. One or more of the casters may be locking casters equipped with brakes 12. The caster brakes 12 may be operated separately and/or in combination in at least the following modes. For example, the brakes may provide a total caster lock to park the mobile patient bed 100, a directional lock on the two rear casters to provide for directional stability during patient transport, and/or a pivot wheel lock on one caster to lock the mobile patient bed 100 pivot wheel when the mobile patient bed 100 is positioned under the laser system.

For example, the mobile patient bed 100 may be configured to pivot underneath the laser system. The mobile patient bed 100 pivot point may be one of the casters (e.g., the front right caster) which may be locked for rolling while still allowing mobile patient bed 100 rotation. In addition, mobile patient bed 100 casters may be selectively locked so that two casters are directionally locked (i.e., they can roll but not turn) while the other two casters are unlocked and may freely rotate. In this "shopping cart" mode, the front casters may freely rotate and the rear casters may be directionally locked, which may aid in transporting the mobile patient bed 100 down halls and/or into position under the laser system. Electronic caster locks may include a manual override in case of power loss. The mobile patient bed 100 may be rolled under the laser system and positioned to align the bridge of the patient's nose with the laser system distal lens using the LED illumination lights of the laser system. The front right mobile patient bed 100 caster wheel may be locked to allow the mobile patient bed 100 to pivot.

The mobile patient bed 100 may include one or more microcontrollers and associated memory and software. In some example embodiments, the firmware may include three microcontrollers, one each for the pendant, joystick, and other mobile patient bed features, respectively. Other configurations (e.g., a single microprocessor for all systems) may be possible. Based on user selection and/or the presence of an active wireless connection between the mobile patient bed 100 and the laser system, the mobile patient bed 100 may be independently controlled through the pendant (e.g., when there is no wireless connection) or control joystick (e.g., when the mobile patient bed 100 is wirelessly connected to the laser system). The microcontrollers may support pendant button input functions to tilt the seat backrest and seat base up and down; to tilt the footrest up and down; to move the Z-axis up and down; and/or to center X and Y stage via a home button, for example. The software may enable and disable some or all caster locks with user input from the pendant button or alternatively from user accessible foot controls. The mobile patient bed 100 may include an on-board battery and an on-board charger that may be used to charge the battery from an external AC power source (e.g., from a wall outlet). The mobile patient bed 100 may also be powered by AC power (e.g., when plugged into a wall outlet).

Figure 2:
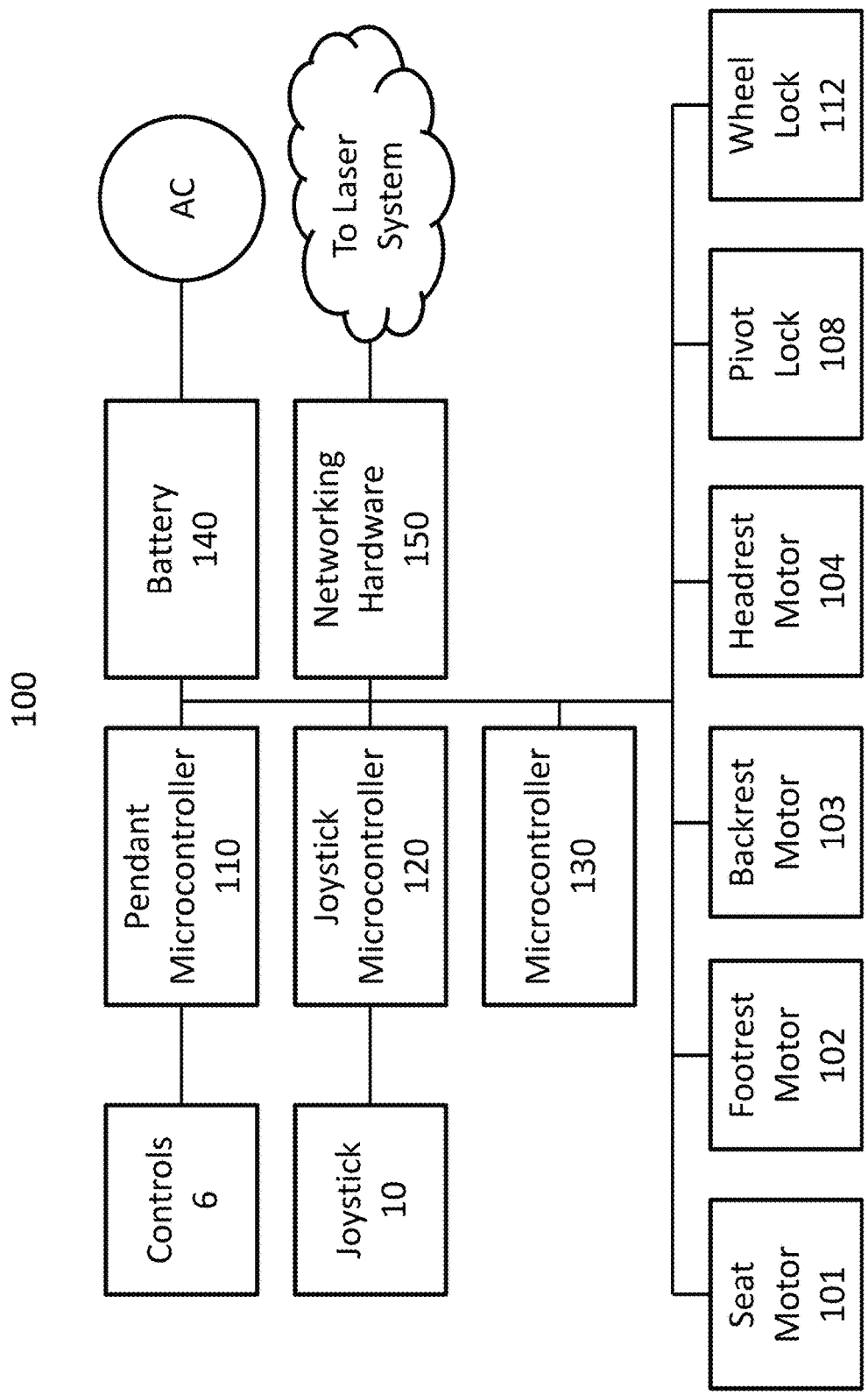
FIG. 2 is a block diagram of a mobile patient bed control system, in accordance with many embodiments.

FIG. 2 shows example mobile patient bed 100 hardware according to an embodiment of the invention. In this example, a pendant microcontroller 110, joystick microcontroller 120, and a microcontroller 130 providing other features are provided. The pendant microcontroller 110 may receive inputs from the controls 6, and the joystick microcontroller 120 may receive inputs from the joystick 10. The microcontrollers 110, 120, 130 may be in communication with at least one seat motor 101 for positioning the seat 1, at least one footrest motor 102 for positioning the footrest 2, at least one backrest motor 103 for positioning the backrest 3, at least one headrest motor 104 for positioning the headrest 4, at least one pivot lock 108 for locking pivoting of one or more casters 8, and/or at least one wheel lock 112 for locking the brakes 12 of one or more casters 8. In some embodiments, some of these elements may be manually actuated without motors. For example, a headrest 4 may be manually positioned in some embodiments. Networking hardware 150 (e.g., a Bluetooth transceiver) may allow one or more of the microcontrollers 110, 120, 130 to communicate with the laser system. For example, the joystick microcontroller 120 may send user inputs to the laser system, and the laser system may control one or more of the motors and/or locks 101, 102, 103, 104, 108, 112 based on the inputs. A battery 140 may supply power to the microcontrollers 110, 120, 130; networking hardware 150, I/O systems 6, 10; and/or motors and locks 101, 102, 103, 104, 108, 112. The battery 140 may be coupled to an AC source (e.g., a wall outlet) for recharging and/or to power the microcontrollers 110, 120, 130; networking hardware 150, I/O systems 6, 10; and/or motors and locks 101, 102, 103, 104, 108, 112. In some embodiments, some or all of the motors 101, 102, 103, 104 may provide complete XYZ freedom of motion and tilting. For example, seat motors 101 may comprise an X motor, a Y motor, a Z motor, and a tilt motor so that the seat 1 may be moved in a direction along the longitudinal axis of the bed 100 and in both axes perpendicular to the longitudinal axis independently of one another. In a further example, the seat 1 may be moved in the X and/or Y direction while the Z position and/or tilt angle is maintained. Likewise, other motors 102, 103, 104 may be provided in sets of X motors, Y motors, and Z motors (e.g., headrest may be moved in a direction along the longitudinal axis of the bed 100 and in both axes perpendicular to the longitudinal axis independently of one another by X headrest motor 104, Y headrest motor 104, and Z headrest motor 104, respectively).

Thus, the bed, and by extension the patient, may be placed in the proper position for each procedure in the various stages of surgery. For example, the patient may be placed supine in some stages, in a Trendelenburg position in other stages, and/or in a seated position in other stages. In some embodiments, the seat 1 may include a sensor such as a strain gauge to detect a person lying on the bed 100. This detection may be communicated to the microcontroller 130.

Mobile Patient Bed Operating Modes

The mobile patient bed 100 may operate in two modes, a standalone mode when not connected to the laser system and a laser surgical platform mode when connected to the laser system or other medical device supporting wireless communication. The mobile patient bed 100 may function through a wireless communication link when connected to the laser system. When not connected to the laser system, the mobile patient bed 100 may function as an independent mobile patient bed.

A standalone mobile patient bed mode may allow the mobile patient bed 100 to be used as a surgical platform for removal of the crystalline lens and implantation of an IOL after laser cataract surgery and to transport patients to and from operating rooms and surgical suites. User input and control may be received through a wired pendant and/or a wireless pendant (e.g., to control the Z position of the bed and articulation of the chair backrest, seat, and/or footrest) and/or foot pedals (e.g., to control bed position and casters) when the mobile patient bed is in standalone mode. The mobile patient bed 100 may be mobile and may be positioned as desired by the user through manually pushing the mobile patient bed 100 on its integral wheels. The mobile patient bed 100 may be equipped with wheel locks to prevent inadvertent motion when locked.

Laser surgical platform mode may allow the mobile patient bed 100 to function as a fully integrated sub-system of the laser system when connected to and controlled by the laser system for performing cataract laser surgery procedures. Connection between the mobile patient bed 100 and the laser system may be through a Bluetooth wireless connection or other wired or wireless connection. When the mobile patient bed 100 is connected to the laser system, the user may control the mobile patient bed 100 (e.g., to adjust bed position in x, y, and z axes) via a control joystick of the laser system and/or control buttons located on the pendant. User inputs may be processed by the laser system, which may control the mobile patient bed 100 to move in accordance with the user inputs.

In laser surgical platform mode, the mobile patient bed 100 may be positioned next to the laser system in one or more positions to accommodate various actions. For example, in a patient load position, the mobile patient bed 100 may be rotated out from under the laser system to allow patient ingress and egress from the mobile patient bed. The mobile patient bed 100 may be in a reclined or chair configuration in this position. This position may have the patient mobile patient bed 100 rotated significantly (e.g., >50° from normal to laser system) out from under the laser system and may provide clearance for the mobile patient bed 100 to be raised into the patient chair configuration.

In a LOI Installation position, the mobile patient bed 100 may be reclined to the patient bed configuration and may be rotated out from under the laser system to a location that allows the physician convenient access to the treatment eye for LOI installation. The user may be responsible for confirming the appropriate position prior to use of the LOI suction ring. For example, this position may have the mobile patient bed 100 rotated approximately 19° out from the patient treatment position (0°)

In a patient treatment position, the mobile patient bed 100 may be rotated to the 0° position under the laser system with the patient treatment eye located directly under the laser aperture for laser treatment. This position may allow the physician to dock and capture the patient to the laser system and perform cataract laser surgery.

An example laser system with which the mobile patient bed 100 may communicate may include one or more systems including host hardware and/or software (e.g., including software that controls code running on top of Windows software on a laser system host computer in some embodiments), a field programmable gate array (FPGA) and associated software that may handle low-level laser delivery and safety modules in the hardware, and a graphical user interface (GUI) engine and/or associated hardware. When connected with the laser system, the mobile patient bed 100 may be predominantly under hardware control via the FPGA. For example, primary safety functions may be provided using hardware on the FPGA. The associated FPGA software may provide the interface between the mobile patient bed 100 and the FPGA, and control of the GUI, error display, and treatment pattern data calculations (e.g., pulse energy at each location). When positioned under and wirelessly connected to the laser system, the mobile patient bed 100 may be a fully integrated sub-system that operates under FPGA control based on user inputs from the mobile patient bed 100 control joystick. The laser system may also receive orientation and alignment data for the mobile patient bed 100 from the mobile patient bed 100 via wireless communication. The user may be able to input Trendelenburg positioning, footrest position, headrest position, etc. via the GUI.

In some embodiments, multiple mobile patient beds 100 may be used with a single laser system. When positioned under and wirelessly connected to the laser system, the mobile patient bed 100, the mobile patient bed's location may be communicated to the laser system and/or detected by the laser system, for example using Bluetooth triangulation. In a situation wherein multiple mobile patient beds 100 are being used with a laser system, any of the beds 100 within wireless range of the laser system may be located and distinguished. Specific beds 100 may be associated with specific patients (e.g., in a memory of the bed 100 itself or the laser system), so that a patient may be located in this manner as well.

The mobile patient bed 100 may be battery powered and may be charged by external electrical connection from an AC power source. The AC power source may be an AC power outlet located at the installation site, for example. During normal use, the mobile patient bed 100 may operate on electrical power supplied from the battery. The mobile patient bed 100 may also be permanently connected to an AC power connection at the installation site for installations where the mobile patient bed is permanently positioned next to the laser system. The mobile patient bed 100 may also be temporarily connected to an AC connection at the installation site if the mobile patient bed battery becomes low on charge during a laser procedure, operating room surgical procedure, recovery period, etc.

In some embodiments, the mobile patient bed 100 may communicate status information to the laser system. For example, the mobile patient bed 100 may send bed status, battery status, actuator positions, detected person on bed, etc. so that the laser system may display this data to a user. Furthermore, the laser system may be able to control operations of the mobile patient bed 100 (e.g., disallowing disconnection of the mobile patient bed 100 during a procedure).

Mobile Patient Bed Subsystems

Figure 3C:
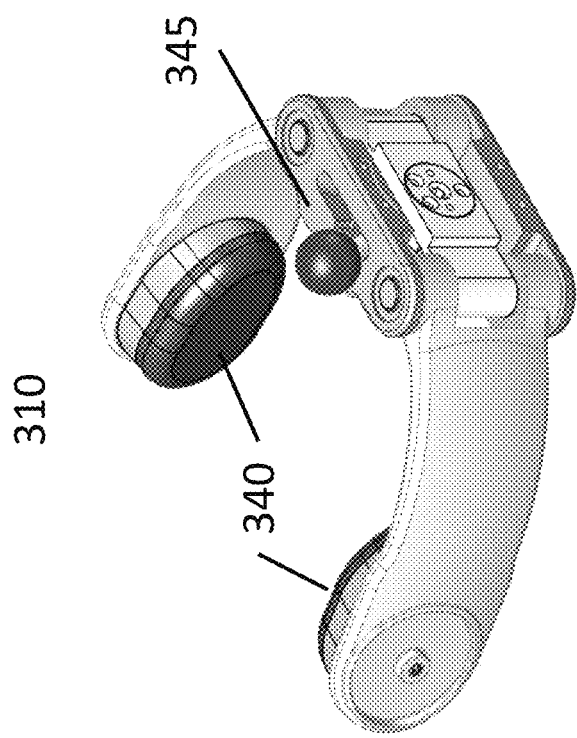

FIGS. 3A-3C show a mobile patient bed headrest 4 according to an embodiment of the invention. Headrest 4 may include a head support 305; side support structure 310;

controls 315, 320, 325 (which may be a subset of controls 6); and guides 330 and/or shafts 335. The head support 305 and side support structure 310 may support a patient's head. The head support 305 may be moved and/or pivoted along guides 330 and/or shafts 335 in the Y pitch, roll, and/or yaw directions using controls 315, 320, 325 (and/or by control from the laser system when the bed 100 is coupled to the laser system). The head support 305 and/or side support structure 315 may be moved in a direction along the longitudinal axis of the bed 100 and in both axes perpendicular to the longitudinal axis independently of one another. The side support structure 315 may include side supports 340 and further controls 345 (which may be a subset of controls 6) for adjusting the side supports 340 to fit around a patient's head and/or pivoting the side supports 340. For example, in some embodiments, the head support 305 and/or side support structure 310 may be pivoted (e.g., +/−5° roll and +/−15° pitch, or some other degree of motion in other embodiments).

FIGS. 4A-4B show mobile patient bed seat motors 101 according to an embodiment of the invention. As noted above, separate seat motors 101 may be provided for each axis of movement to allow the mobile patient bed 100 to be precisely and accurately positioned with respect to a laser system. For example, an X motor 101X, a Y motor 101Y, and a Z motor 101Z may be provided as shown. Thus, in one example situation, the bed 100 may be located by the laser system (e.g., via the laser system using Bluetooth triangulation and/or sensing reflective targets on the bed 100 and/or floor), and the bed 100 position may be finely adjusted in each of the X, Y, and Z directions separately and independently.

Figure 5:
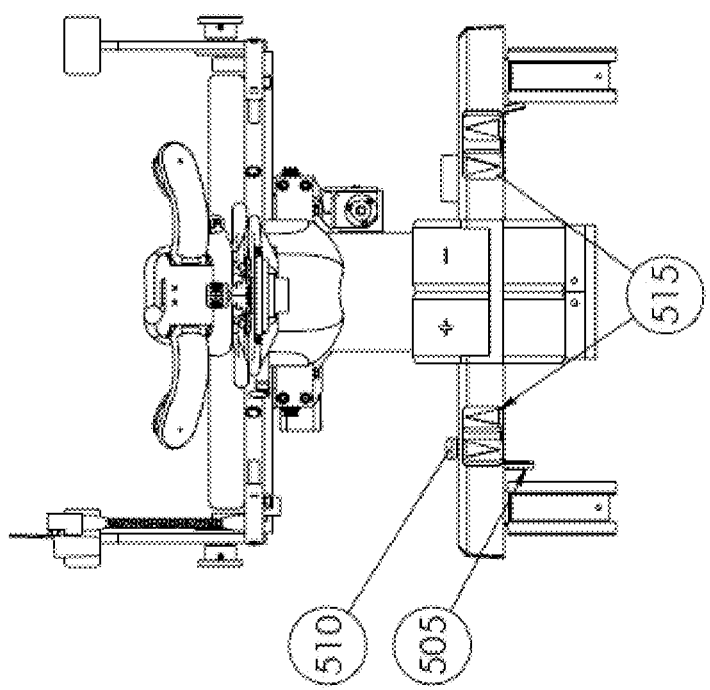
FIG. 5 is a perspective view showing mobile patient bed control elements, in accordance with many embodiments.
Figure 6D:
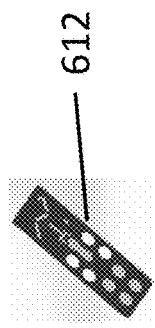
FIGS. 6A-6G show a mobile patient bed pendant, in accordance with many embodiments.
Figure 6E:
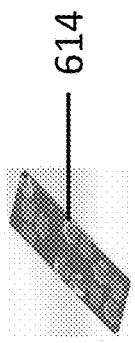
Figure 6F:
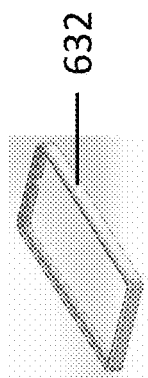
Figure 6G:
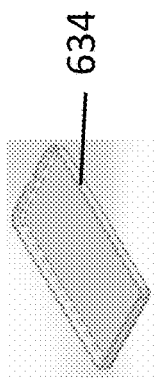
Figure 6A:
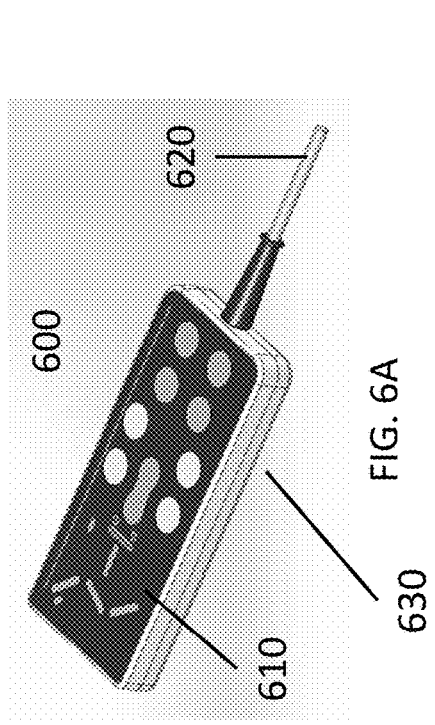
Figure 6B:
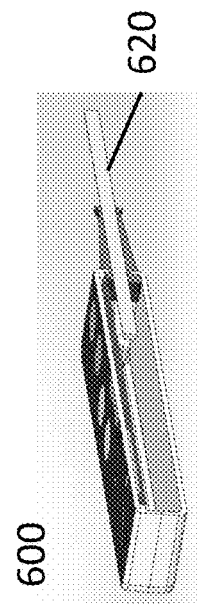
Figure 6C:
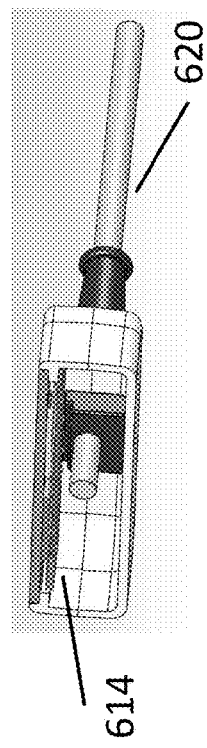
Figure 7:
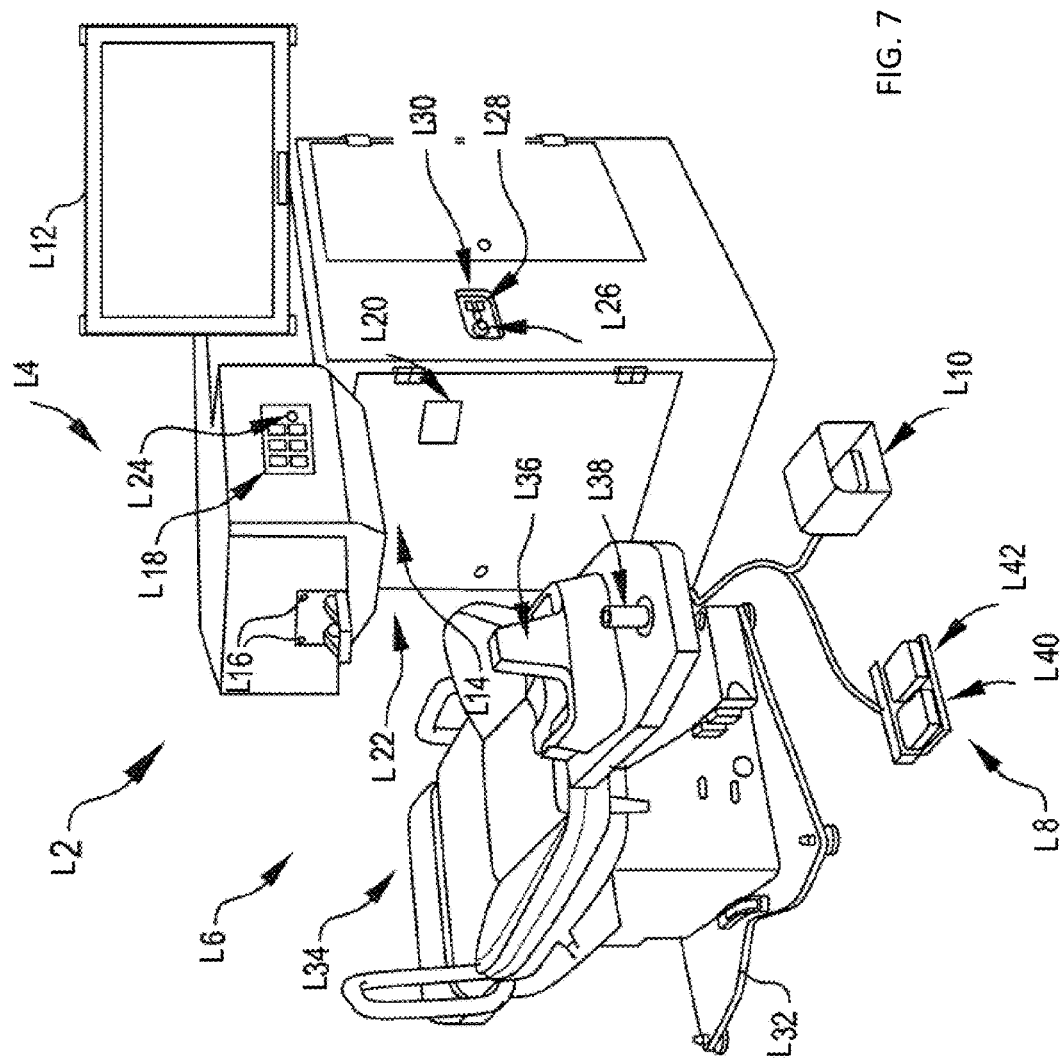
FIG. 7 is a perspective view showing a laser eye surgery system, in accordance with many embodiments.

FIG. 5 is a perspective view showing mobile patient bed control elements according to an embodiment of the invention. Some controls 6 may be foot-actuated controls located on a frame of the mobile patient bed 100. For example, brake pedals 505 may be provided in multiple locations and may enable and/or disable total lock of brakes 12. A latching toggle switch 510 may toggle latching and/or control illumination on other controls 6. Z-axis pedals 515 may be provided in separate locations and may control movement of the bed 100 in the Z axis. Those of ordinary skill in the art will appreciate that other control 6 configurations may be possible. FIG. 5 merely presents one possible arrangement for a subset of the controls 6 of the mobile patient bed 100.

FIGS. 6A-6G show a mobile patient bed pendant 600 according to an embodiment of the invention. The pendant 600 may comprise a user interface 610 and may connect to the mobile patient bed 100 via a cable 620. The user interface 610 may include a front panel 612 with buttons that may be illuminated by light pipes in a printed circuit board 614. The printed circuit board 614 may register button presses and send data associated therewith to the mobile patient bed 100 via the cable 620. The printed circuit board 614 may receive power for illuminating the light pipes from the mobile patient bed 100 via the cable 620, as well. The user interface 610 may be housed in a housing 630. The housing 630 may include an open front panel 632 through which the buttons may protrude and a closed back panel 634. Those of ordinary skill in the art will appreciate that other pendant 600 configurations may be possible. FIG. 6 merely presents one possible arrangement for a pendant 600 providing at least a subset of the controls 6 of the mobile patient bed 100.

Laser System

Figure 8:
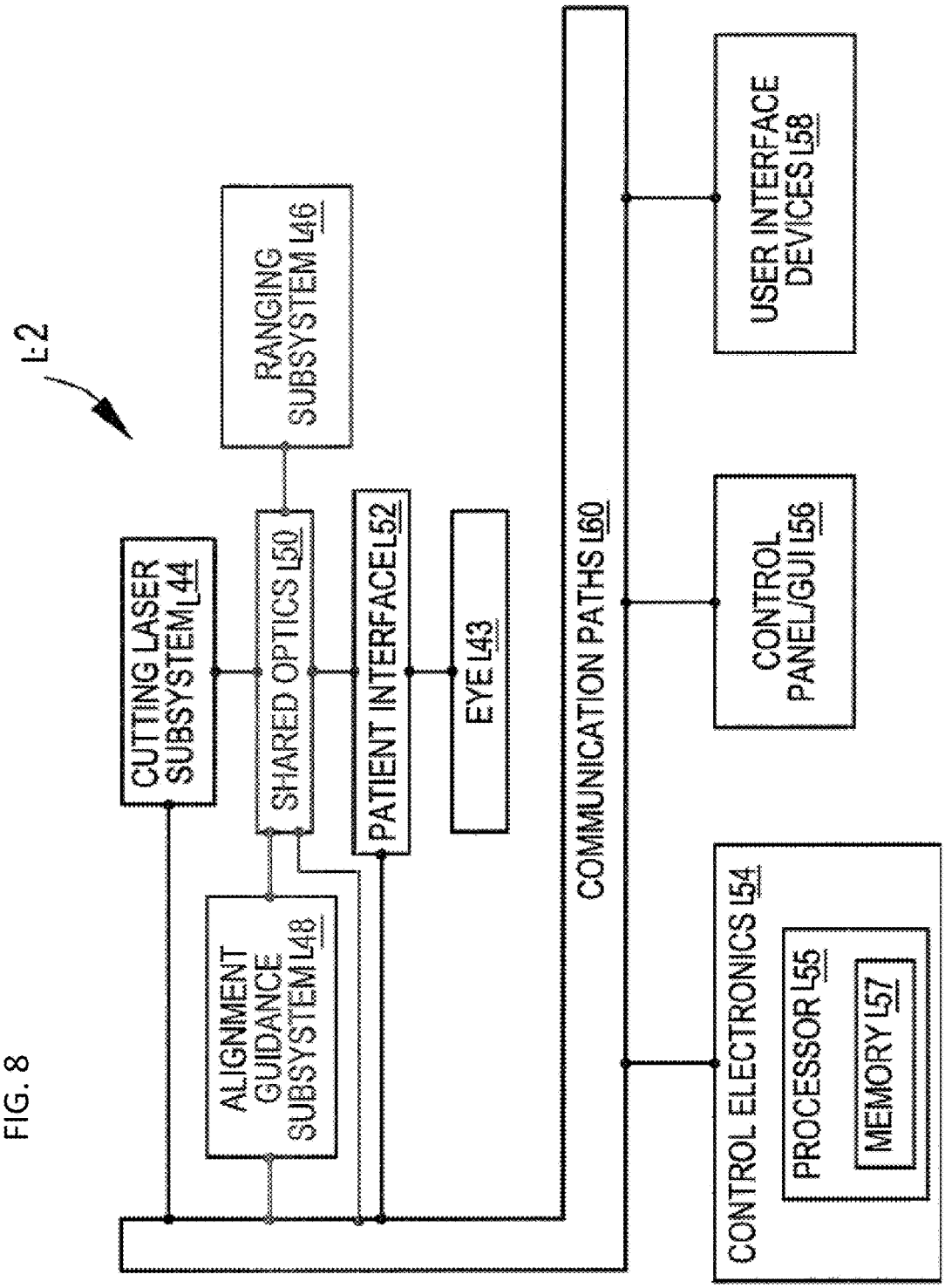
FIG. 8 is a simplified block diagram showing a top level view of the configuration of a laser eye surgery system, in accordance with many embodiments.

As described above, the mobile patient bed 100 may be selectively coupled to a system such as a laser system. FIGS. 8 and 9 illustrate an example laser system. Those of ordinary skill in the art will appreciate that many other laser system configurations may be possible, and/or that the mobile patient bed 100 may be selectively coupled to other types of systems entirely.

FIG. 8 shows a laser eye surgery system L2, in accordance with many embodiments, operable to form precise incisions in the cornea, in the lens capsule, and/or in the crystalline lens nucleus. The system L2 may include a main unit L4, a patient chair L6, a dual function footswitch L8, and a laser footswitch L10. The patient chair L6 may be a fixed chair or, in accordance with the systems and methods described herein, may be the mobile patient bed 100.

The main unit L4 may include many primary subsystems of the system L2. For example, externally visible subsystems may include a touch-screen control panel L12, a patient interface assembly L14, patient interface vacuum connections L16, a docking control keypad L18, a patient interface radio frequency identification (RFID) reader L20, external connections L22 (e.g., network, video output, footswitch, USB port, door interlock, and AC power), laser emission indicator L24, emergency laser stop button L26, key switch L28, and USB data ports L30.

The patient chair L6 may include a base L32, a patient support bed L34, a headrest L36, a positioning mechanism, and a patient chair joystick control L38 disposed on the headrest L36. The positioning control mechanism may be coupled between the base L32 and the patient support bed L34 and headrest L36. The patient chair L6 may be configured to be adjusted and oriented in three axes (x, y, and z) using the patient chair joystick control L38. The headrest L36 and a restrain system (not shown, e.g., a restraint strap engaging the patient's forehead) may stabilize the patient's head during the procedure. The headrest L36 may include an adjustable neck support to provide patient comfort and to reduce patient head movement. The headrest L36 may be configured to be vertically adjustable to enable adjustment of the patient head position to provide patient comfort and to accommodate variation in patient head size.

The patient chair L6 may allow for tilt articulation of the patient's legs, torso, and head using manual adjustments. The patient chair L6 may accommodate a patient load position, a suction ring capture position, and a patient treat position. In the patient load position, the chair L6 may be rotated out from under the main unit L4 with the patient chair back in an upright position and patient footrest in a lowered position. In the suction ring capture position, the chair may be rotated out from under the main unit L4 with the patient chair back in reclined position and patient footrest in raised position. In the patient treat position, the chair may be rotated under the main unit L4 with the patient chair back in reclined position and patient footrest in raised position.

The patient chair L6 may be equipped with a "chair enable" feature to protect against unintended chair motion. The patient chair joystick L38 may be enabled in at least two ways. First, the patient chair joystick L38 may incorporate a "chair enable" button located on the top of the joystick. Control of the position of the patient chair L6 via the joystick L38 may be enabled by continuously pressing the "chair enable" button. Alternately, the left foot switch L40 of the dual function footswitch L8 may be continuously depressed to enable positional control of the patient chair L6 via the joystick L38.

In many embodiments, the patient control joystick L38 may be a proportional controller. For example, moving the joystick a small amount may be used to cause the chair to move slowly. Moving the joystick a large amount may be used to cause the chair to move faster. Holding the joystick at its maximum travel limit may be used to cause the chair to move at the maximum chair speed. The available chair speed may be reduced as the patient approaches the patient interface assembly L14.

The emergency stop button L26 may be pushed to stop emission of all laser output, release vacuum that couples the patient to the system L2, and disable the patient chair 6. The stop button L26 may be located on the system front panel, next to the key switch L28.

The key switch L28 may be used to enable the system L2. When in a standby position, the key may be removed and the system may be disabled. When in a ready position, the key may enable power to the system L2.

The dual function footswitch L8 may be a dual footswitch assembly that may include the left foot switch L40 and a right foot switch L42. The left foot switch L40 may be the "chair enable" footswitch. The right footswitch L42 may be a "vacuum ON" footswitch that may enable vacuum to secure a liquid optics interface suction ring to the patient's eye. The laser footswitch L10 may be a shrouded footswitch that activates the treatment laser when depressed while the system is enabled.

In many embodiments, the system L2 may include external communication connections. For example, the system L2 may include a network connection (e.g., an RJ45 network connection) for connecting the system L2 to a network. The network connection may be used to enable network printing of treatment reports, remote access to view system performance logs, and remote access to perform system diagnostics. The system L2 may include a video output port (e.g., HDMI) that may be used to output video of treatments performed by the system L2. The output video may be displayed on an external monitor for, for example, viewing by family members and/or training. The output video may also be recorded for, for example, archival purposes. The system L2 may include one or more data output ports (e.g., USB) to, for example, enable export of treatment reports to a data storage device. The treatments reports stored on the data storage device may then be accessed at a later time for any suitable purpose such as, for example, printing from an external computer in the case where the user without access to network based printing.

FIG. 8 shows a simplified block diagram of the system L2 coupled with a patient eye L43. The patient eye L43 comprises a cornea, a lens, and an iris. The iris defines a pupil of the eye L43 that may be used for alignment of eye L43 with system L2. The system L2 may include a cutting laser subsystem L44, a ranging subsystem L46, an alignment guidance system L48, shared optics L50, a patient interface L52, control electronics L54, a control panel/GUI L56, user interface devices L58, and communication paths L60. The control electronics L54 may be operatively coupled via the communication paths L60 with the cutting laser subsystem L44, the ranging subsystem L46, the alignment guidance subsystem L48, the shared optics L50, the patient interface L52, the control panel/GUI L56, and the user interface devices L58.

In many embodiments, the cutting laser subsystem L44 may incorporate femtosecond (FS) laser technology. By using femtosecond laser technology, a short duration (e.g., approximately 10-13 seconds in duration) laser pulse (with energy level in the micro joule range) may be delivered to a tightly focused point to disrupt tissue, thereby substantially lowering the energy level required as compared to the level required for ultrasound fragmentation of the lens nucleus and as compared to laser pulses having longer durations.

The cutting laser subsystem L44 may produce laser pulses having a wavelength suitable to the configuration of the system L2. As a non-limiting example, the system L2 may be configured to use a cutting laser subsystem L44 that produces laser pulses having a wavelength from 1020 nm to 1050 nm. For example, the cutting laser subsystem L44 may have a diode-pumped solid-state configuration with a 1030 (+/−5) nm center wavelength.

The cutting laser subsystem L44 may include control and conditioning components. For example, such control components may include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components may include an adjustable zoom assembly to adapt the beam containing the laser pulses to the characteristics of the system L2 and a fixed optical relay to transfer the laser pulses over a distance while accommodating laser pulse beam positional and/or directional variability, thereby providing increased tolerance for component variation.

The ranging subsystem L46 may be configured to measure the spatial disposition of eye structures in three dimensions. The measured eye structures may include the anterior and posterior surfaces of the cornea, the anterior and posterior portions of the lens capsule, the iris, and the limbus. In many embodiments, the ranging subsystem L46 may use optical coherence tomography (OCT) imaging. As a non-limiting example, the system L2 can be configured to use an OCT imaging system employing wavelengths from 780 nm to 970 nm. For example, the ranging subsystem L46 may include an OCT imaging system that employs a broad spectrum of wavelengths from 810 nm to 850 nm. Such an OCT imaging system may employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem L48 may include a laser diode or gas laser that produces a laser beam used to align optical components of the system L2. The alignment guidance subsystem L48 may include LEDs or lasers that produce a fixation light to assist in aligning and stabilizing the patient's eye during docking and treatment. The alignment guidance subsystem L48 may include a laser or LED light source and a detector to monitor the alignment and stability of the actuators used to position the beam in X, Y, and Z. The alignment guidance subsystem L48 may include a video system that can be used to provide imaging of the patient's eye to facilitate docking of the patient's eye L43 to the patient interface L52. The imaging system provided by the video system may also be used to direct via the GUI the location of cuts. The imaging provided by the video system may additionally be used during the laser eye surgery procedure to monitor the progress of the procedure, to track movements of the patient's eye L43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface L52 may be used to restrain the position of the patient's eye L43 relative to the system L2. In many embodiments, the patient interface L52 may employ a suction ring that may be vacuum attached to the patient's eye L43. The suction ring may then be coupled with the patient interface L52, for example, using vacuum to secure the suction ring to the patient interface L52. In many embodiments, the patient interface L52 may include an optically transmissive structure having a posterior surface that is displaced vertically from the anterior surface of the patient's cornea, and a region of a suitable liquid (e.g., a sterile buffered saline solution (BSS) such as Alcon BSS (Alcon Part Number 351-55005-1) or equivalent) may be disposed between and in contact with the posterior surface and the patient's cornea and may form part of a transmission path between the shared optics L50 and the patient's eye L43. The optically transmissive structure may comprise a lens L96 having one or more curved surfaces. Alternatively, the patient interface L22 may comprise an optically transmissive structure having one or more substantially flat surfaces such as a parallel plate or wedge. In many embodiments, the patient interface lens may be disposable and may be replaced at any suitable interval, such as before each eye treatment.

The control electronics L54 may control the operation of and may receive input from the cutting laser subsystem L44, the ranging subsystem L46, the alignment guidance subsystem L48, the patient interface L52, the control panel/GUI L56, and the user interface devices L58 via the communication paths L60. The communication paths L60 may be implemented in any suitable configuration, including any suitable shared or dedicated communication paths between the control electronics L54 and the respective system components.

The control electronics L54 may include any suitable components, such as one or more processor, one or more field-programmable gate array (FPGA), and one or more memory storage devices. In many embodiments, the control electronics L54 may control the control panel/GUI L56 to provide for pre-procedure planning according to user specified treatment parameters as well as to provide user control over the laser eye surgery procedure.

The control electronics L54 may comprise a processor/controller L55 (referred to herein as a processor) that may be used to perform calculations related to system operation and provide control signals to the various system elements. A computer readable medium L57 (also referred to as a database or a memory) may be coupled to the processor L55 in order to store data used by the processor and other system elements. The processor L55 may interact with the other components of the system as described more fully throughout the present specification and other documents incorporated by reference herein. In an embodiment, the memory L57 may include a look up table that can be utilized to control one or more components of the laser system as described herein.

The processor L55 may be a general purpose microprocessor configured to execute instructions and data, such as a Pentium processor manufactured by the Intel Corporation of Santa Clara, California. It may also be an Application Specific Integrated Circuit (ASIC) that embodies at least part of the instructions for performing the method in accordance with the embodiments of the present disclosure in software, firmware and/or hardware. As an example, such processors may include dedicated circuitry, ASICs, combinatorial logic, other programmable processors, combinations thereof, and the like.

The memory L57 may be local or distributed as appropriate to the particular application. Memory L57 may include a number of memories including a main random access memory (RAM) for storage of instructions and data during program execution and a read only memory (ROM) in which fixed instructions are stored. Thus, memory L57 may provide persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices L58 may include any suitable user input device suitable to provide user input to the control electronics L54. For example, the user interface devices L58 may include devices such as, for example, the dual function footswitch L8, the laser footswitch L10, the docking control keypad L18, the patient interface radio frequency identification (RFID) reader L20, the emergency laser stop button L26, the key switch L28, and the patient chair joystick control L38. All patents and patent applications cited herein are hereby incorporated by reference in their entirety. The use of the terms ""a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention. The use of the terms shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention. While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

In addition, it should be understood that any figures that highlight the functionality and advantages are presented for example purposes only. The disclosed methodology and system are each sufficiently flexible and configurable such that they may be utilized in ways other than that shown.

Finally only claims that include the express language "means for" or "step for" should be interpreted under 35 U.S.C. 112(f). Claims that do not expressly include the phrase "means for" or "step for" are not to be interpreted under 35 U.S.C. 112(f).

What is claimed is:

1. A mobile patient bed for moving a patient between at least two locations during a medical procedure, the mobile patient bed comprising:
   at least one user control configured receive user commands;
   a communication device configured to selectively couple the mobile patient bed to at least one medical system;
   at least one processor configured to:
      in response to the mobile patient bed being coupled to the at least one medical system, receive a medical system command via the communication device and process the medical system command, and refrain from processing user commands received from the at least one user control; and
      in response to the mobile patient bed not being coupled to the at least one medical system, receive and process a user command received from the at least one user control;
   a seat; and
   a plurality of motors configured to move the seat in a plurality of degrees of freedom, wherein the moving of the seat is performed in response to the processed medical system command or the processed user command.

2. The mobile patient bed of claim 1, further comprising a headrest configured to move in a plurality of degrees of freedom.

3. The mobile patient bed of claim 1, wherein the communication device comprises a Bluetooth transceiver or other wireless transceiver.

4. The mobile patient bed of claim 1, wherein the at least one user control comprises a pendant, a handle, a foot pedal, or a combination thereof.

5. The mobile patient bed of claim 1, further comprising a user interface device coupled to the at least one processor and configured to input a user command to the at least one medical system via the communication device.

6. The mobile patient bed of claim 1, further comprising a seat sensor configured to detect a person on the seat.

7. A system comprising: at least one mobile patient bed of claim 1; and the medical system.

8. The system of claim 7, wherein the medical system is configured to assign a separate identity to each at least one mobile patient bed.

9. The system of claim 7, wherein the communication device is configured to send status information to the medical system.

10. The system of claim 7, wherein the medical system is configured to control the at least one processor via a command sent to the communication device.

11. A system comprising:
   a medical system;
   at least one mobile patient bed of claim for moving a patient between at least two locations during a medical procedure, the mobile patient bed comprising:
      a communication device configured to selectively couple the mobile patient bed to at least one medical system;
      at least one processor configured to: receive a medical system command via the communication device and process the medical system command when the mobile patient bed is coupled to the at least one medical system, receive and process a user command when the mobile patient bed is not coupled to the at least one medical system, and refrain from processing the user command when the mobile patient bed is coupled to the at least one medical system;
      a seat and
      a plurality of motors configured to move the seat in a plurality of degrees of freedom, wherein the moving of the seat is performed in response to the processed medical system command or the processed user command; and
   wherein the medical system is configured to determine a location of the at least one mobile patient bed via a signal received from the communication device of the at least one mobile patient bed.

12. The system of claim 11, wherein: the medical system comprises a plurality of receivers configured to receive the signal; and determining the location of the at least one mobile patient bed comprises performing triangulation based on the signal received at each of the plurality of receivers.

13. A method of performing a medical procedure, the method comprising:
   moving a mobile patient bed between at least two locations during a medical procedure;
   in at least one of the at least two locations, coupling, with a communication device of the mobile patient bed, the mobile patient bed to at least one medical system;

in response to the mobile patient bed being coupled to the at least one medical system, receiving, via at least one processor, a medical system command via the communication device and processing, by the at least one processor, the medical system command;

in response to the mobile patient bed being coupled to the at least one medical system, refraining, by the at least one processor, from processing a user command received from at least one user control of the mobile patient bed;

in at least another one of the at least two locations, decoupling the mobile patient bed from the at least one medical system;

in response to the mobile patient bed not being coupled to the at least one medical system, receiving and processing, by the at least one processor, a user command received from the at least one user control of the mobile patient bed; and in at least one of the at least two locations, moving, with a plurality of motors of the mobile patient bed, a seat of the mobile patient bed in a plurality of degrees of freedom, wherein the moving of the seat is performed in response to the processed medical system command or the processed user command.

14. The method of claim 13, further comprising determining, with the medical system, a location of the at least one mobile patient bed via a signal received from the communication device of the at least one mobile patient bed when the mobile patient bed is coupled to the at least one medical system.

15. The method of claim 14, wherein determining the location of the at least one mobile patient bed comprises performing triangulation based on the signal being received at each of a plurality of receivers of the medical system.

16. The method of claim 13, further comprising assigning, with the medical system, a separate identity to each at least one mobile patient bed when the mobile patient bed is coupled to the at least one medical system.

17. The method of claim 13, further comprising detecting, with a seat sensor, a person on the seat.

18. The method of claim 13, further comprising sending, with the communication device, status information to the medical system.

19. The method of claim 13, further comprising controlling, with the medical system, the at least one processor via a command sent to the communication device.

* * * * *